(12) United States Patent
Thompson-Nauman et al.

(10) Patent No.: US 9,138,157 B2
(45) Date of Patent: Sep. 22, 2015

(54) METHOD AND APPARATUS FOR CARDIAC FUNCTION MONITORING

(71) Applicant: Medtronic, Inc., Minneapolis, MN (US)

(72) Inventors: Amy E. Thompson-Nauman, Ham Lake, MN (US); Michael J Ebert, Fridley, MN (US); Rick D McVenes, Isanti, MN (US); Nathan A Grenz, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 148 days.

(21) Appl. No.: 14/056,003

(22) Filed: Oct. 17, 2013

(65) Prior Publication Data

US 2015/0112216 A1    Apr. 23, 2015

(51) Int. Cl.
    *A61N 1/37*    (2006.01)
    *A61B 5/0402*   (2006.01)

(52) U.S. Cl.
    CPC .................................. *A61B 5/0402* (2013.01)

(58) Field of Classification Search
    CPC ......................... A61B 2018/00666; A61N 1/37
    See application file for complete search history.

(56) References Cited

U.S. PATENT DOCUMENTS

| | | | |
|---|---|---|---|
| 8,052,611 B2 | 11/2011 | Wariar et al. | |
| 8,126,554 B2 | 2/2012 | Kane et al. | |
| 8,321,013 B2 | 11/2012 | Darvish et al. | |
| 8,401,627 B1 | 3/2013 | Farazi et al. | |
| 8,428,729 B2 | 4/2013 | Schwartz et al. | |
| 2006/0167365 A1* | 7/2006 | Bharmi | 600/517 |
| 2006/0217771 A1 | 9/2006 | Soykan et al. | |
| 2012/0197231 A1 | 8/2012 | Kane et al. | |
| 2012/0277546 A1* | 11/2012 | Soykan et al. | 600/301 |

* cited by examiner

*Primary Examiner* — Christopher D Koharski
*Assistant Examiner* — Natasha Patel
(74) *Attorney, Agent, or Firm* — Michael C. Soldner

(57) ABSTRACT

A method and medical device for monitoring cardiac function in a patient that includes a plurality of electrodes to deliver cardiac pacing therapy, and a processor configured to determine a pacing threshold in response to initial delivery of the pacing therapy, determine whether there is a change in the pacing threshold during initial delivery of the pacing therapy, adjust a delivery parameter of the pacing therapy in response to determining the change in the pacing threshold during initial delivery of the pacing therapy, determine whether there is an increase in the pacing threshold during delivery of the adjusted pacing therapy, and determine hypokalemia in response to the increase in the pacing threshold during delivery of the adjusted pacing therapy being present.

23 Claims, 10 Drawing Sheets

METHOD AND APPARATUS FOR CARDIAC FUNCTION MONITORING

RELATED APPLICATION

Cross-reference is hereby made to commonly assigned U.S. patent application Ser. No. 14/056,053, filed on even date herewith entitled "METHOD AND APPARATUS FOR CARDIAC FUNCTION MONITORING", and incorporated by reference in it's entirety.

FIELD OF THE DISCLOSURE

The disclosure relates generally to medical devices and, in particular, to a method and apparatus for detecting homeostasis variations for monitoring cardiac function.

BACKGROUND

Homeostasis refers to the ability or tendency of an organism or a cell to maintain internal equilibrium by adjusting its physiological processes to maintain equilibrium or stability in the normal physiological states of the organism. In cardiac patients, homeostasis can involve maintaining a constant condition of appropriate fluid and electrolyte loads within and outside of the cells of the patient's heart. Potassium, for example, which is a necessary electrolyte of the heart, facilitates nerve impulse conduction and the contraction of the heart, along with cell membrane function and proper enzyme activity. Hypokalemia is a condition in which there are below normal levels of potassium in the blood serum, while hyperkalemia is a condition in which there are above normal levels of potassium in the blood serum. Both hyperkalemia and hypokalemia can occasionally provoke or indicate cardiac arrhythmias. Therefore, it is important that potassium levels be kept in a proper (homeostatic) balance for the maintenance of cardiac health. What is needed is a method and apparatus for monitoring of cardiac homeostasis to more effectively enable the earliest detection and accurate monitoring of potentially life-threatening arrhythmia conditions and/or progressive cardiac disease states.

DETAILED DESCRIPTION

In the following description, references are made to illustrative embodiments. It is understood that other embodiments may be utilized without departing from the scope of the disclosure. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

A medical device according to the present invention may include one or more of the features, structures, methods, or combinations thereof described hereinbelow. For example, a status monitor, cardiac monitor, cardiac stimulator, or other type of implantable or patient-external medical device may be implemented to include one or more of the advantageous features and/or processes described below. It is intended that such a monitor, stimulator, or other external, implanted or partially implanted device need not include all of the features described herein, but may be implemented to include selected features that provide for useful structures and/or functionality. Such a device may be implemented to provide a variety of therapeutic or diagnostic functions.

Figure 1:
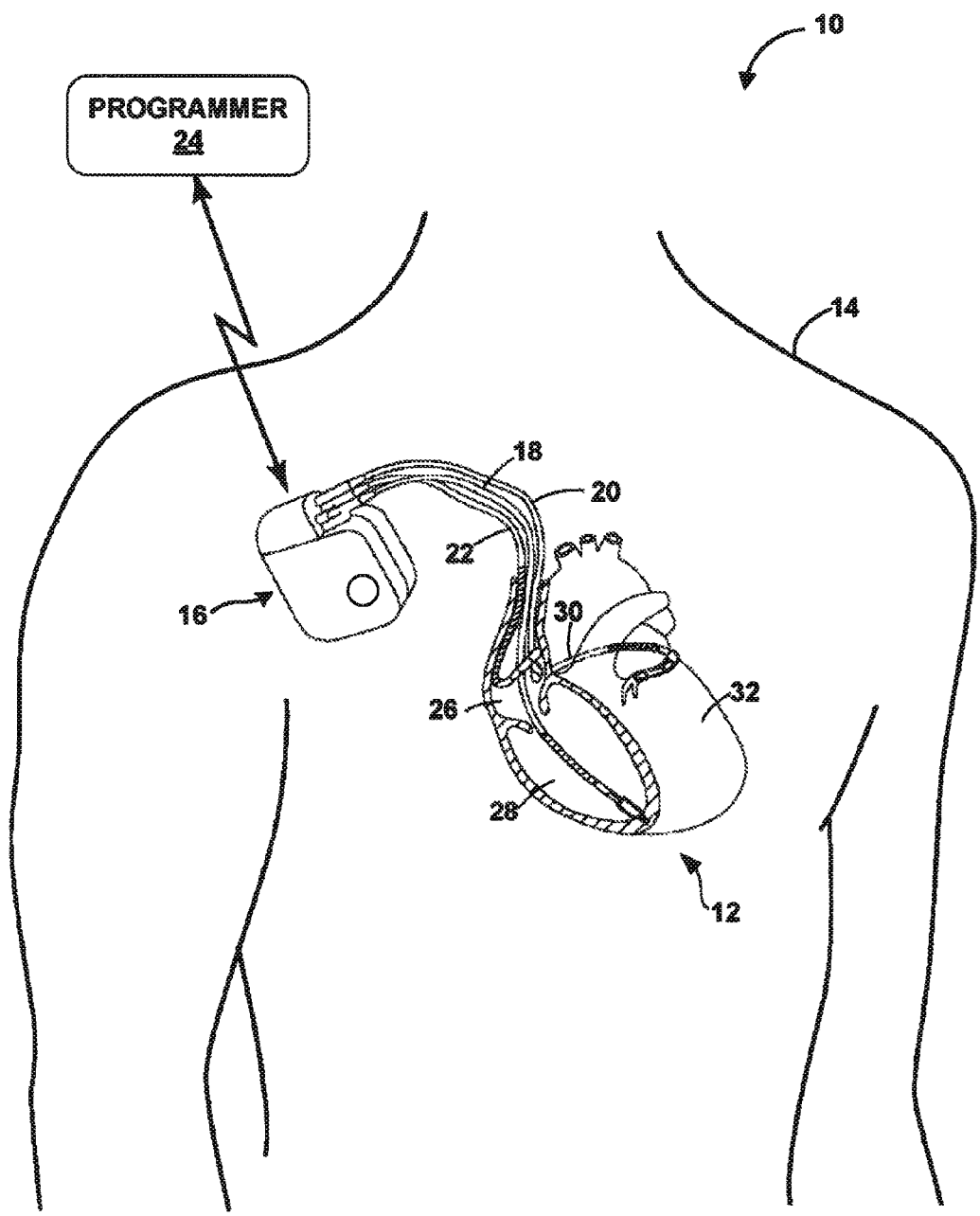
FIG. 1 is a functional block diagram of an exemplary medical device for monitoring cardiac function according to an embodiment of the present disclosure.

FIG. 1 is a conceptual diagram illustrating an exemplary system 10 for monitoring cardiac function according to an embodiment of the present disclosure. System 10 includes implantable medical device (IMD) 16, which is connected to leads 18, 20, and 22 and is communicatively coupled to a programmer 24. IMD 16 senses electrical signals attendant to the depolarization and repolarization of heart 12, e.g., a cardiac electrogram (EGM), via electrodes on one or more leads 18, 20 and 22 or the housing of IMD 16. IMD 16 may also deliver therapy in the form of electrical signals to heart 12 via electrodes located on one or more leads 18, 20 and 22 or a housing of IMD 16, the therapy may be pacing, cardioversion and/or defibrillation pulses.

Leads 18, 20, 22 extend into the heart 12 of patient 14 to sense electrical activity of heart 12 and/or deliver electrical stimulation to heart 12. In the example shown in FIG. 1, right ventricular (RV) lead 18 extends through one or more veins (not shown), the superior vena cava (not shown), and right atrium 26, and into right ventricle 28. Left ventricular (LV) coronary sinus lead 20 extends through one or more veins, the vena cava, right atrium 26, and into the coronary sinus 30 to a region adjacent to the free wall of left ventricle 32 of heart 12. Right atrial (RA) lead 22 extends through one or more veins and the vena cava, and into the right atrium 26 of heart 12.

In some examples, programmer 24 takes the form of a handheld computing device, computer workstation or networked computing device that includes a user interface for presenting information to and receiving input from a user. A user, such as a physician, technician, surgeon, electro-physiologist, or other clinician, may interact with programmer 24 to retrieve physiological or diagnostic information from IMD 16. A user may also interact with programmer 24 to program IMD 16, e.g., select values for operational parameters of the IMD.

IMD 16 and programmer 24 may communicate via wireless communication using any techniques known in the art. Examples of communication techniques may include, for example, low frequency or radiofrequency (RF) telemetry. Other techniques are also contemplated. In some examples, programmer 24 may include a programming head that may be placed proximate to the patient's body near the IMD 16 implant site in order to improve the quality or security of communication between IMD 16 and programmer 24. In some examples, programmer 24 may be located remotely from IMD 16, and communicate with IMD 16 via a network. Programmer 24 may also communicate with one or more other external devices using a number of known communication techniques, both wired and wireless.

Figure 2:
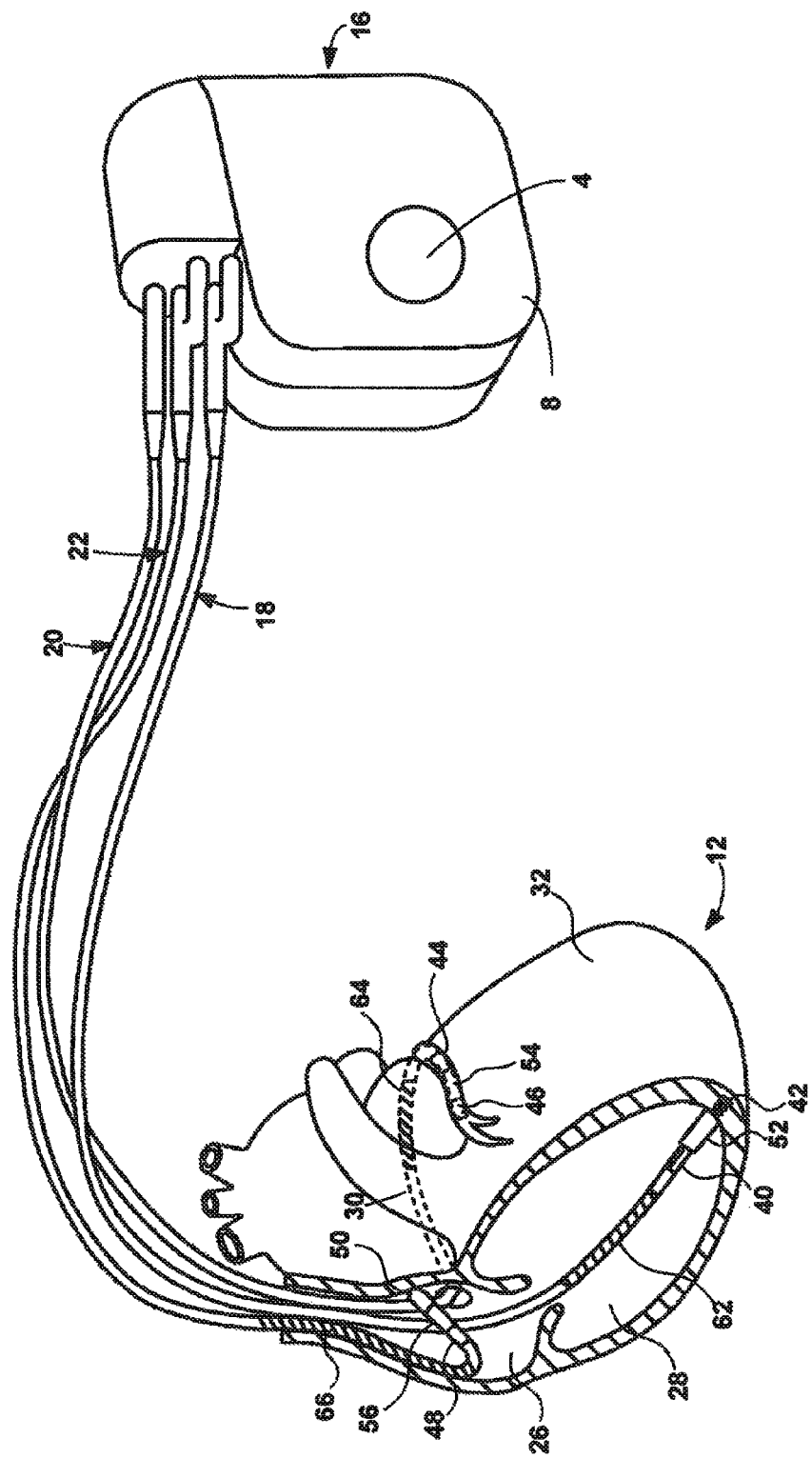
FIG. 2 is a conceptual diagram of the medical device of FIG. 1 according to an embodiment of the present disclosure.

FIG. 2 is a conceptual diagram illustrating IMD 16 and leads 18, 20 and 22 of system 10 in greater detail. In the illustrated example, bipolar electrodes 40 and 42 are located adjacent to a distal end of lead 18. In addition, bipolar electrodes 44 and 46 are located adjacent to a distal end of lead 20, and bipolar electrodes 48 and 50 are located adjacent to a distal end of lead 22. In alternative embodiments, not shown in FIG. 2, one or more of leads 18, 20 and 22, e.g., left-ventricular lead 20, may include quadrapole electrodes located adjacent to a distal end of the lead.

In the illustrated example, electrodes 40, 44 and 48 take the form of ring electrodes, and electrodes 42, 46 and 50 may take the form of extendable helix tip electrodes mounted retractably within insulative electrode heads 52, 54 and 56, respectively. Leads 18, 20, 22 also include elongated electrodes 62, 64, 66, respectively, which may take the form of a coil. In some examples, each of electrodes 40, 42, 44, 46, 48, 50, 62, 64 and 66 is electrically coupled to a respective conductor within the lead body of its associated lead 18, 20, 22 and thereby coupled to circuitry within IMD 16.

In some examples, IMD 16 includes one or more housing electrodes, such as housing electrode 4 illustrated in FIG. 2, which may be formed integrally with an outer surface of hermetically-sealed housing 8 of IMD 16 or otherwise coupled to housing 8. In some examples, housing electrode 4 is defined by an uninsulated portion of an outward facing portion of housing 8 of IMD 16. Other divisions between insulated and uninsulated portions of housing 8 may be employed to define two or more housing electrodes. In some examples, a housing electrode comprises substantially all of housing 8.

As described in further detail with reference to FIG. 3, housing 8 encloses a signal generator that generates therapeutic stimulation, such as cardiac pacing, cardioverison and defibrillation pulses, as well as a sensing module for sensing electrical signals attendant to the depolarization and repolarization of heart 12. IMD 16 senses electrical signals attendant to the depolarization and repolarization of heart 12 via electrodes 4, 40, 42, 44, 46, 48, 50, 62, 64 and 66. IMD 16 may sense such electrical signals via any bipolar combination of electrodes 40, 42, 44, 46, 48, 50, 62, 64 and 66. Furthermore, any of the electrodes 40, 42, 44, 46, 48, 50, 62, 64 and 66 may be used for unipolar sensing in combination with housing electrode 4.

The illustrated numbers and configurations of leads 18, 20 and 22 and electrodes are merely examples. Other configurations, i.e., number and position of leads and electrodes, are possible. In some examples, system 10 may include an additional lead or lead segment having one or more electrodes positioned at different locations in the cardiovascular system for sensing and/or delivering therapy to patient 14. For example, instead of or in addition to intercardiac leads 18, 20 and 22, system 10 may include one or more epicardial or subcutaneous leads not positioned within the heart. In some examples, system 10 may include an additional lead that carries an acoustic sensor positioned such that signals generated by the acoustic sensor include respiratory sounds in response to a cough or diaphragm movement.

Furthermore, in some examples, IMD 16 need not be coupled to any leads, need not provide electrical stimulation or other therapy, and/or need not sense electrical cardiac signals. In some examples, the techniques described herein may be implemented in a leadless monitoring device, such as a Reveal® insertable monitor available from Medtronic, Inc. of Minneapolis, Minn. Such a device may be configured to include additional sensors, such as an acoustic sensor and/or, an activity sensor, and provide the functionality described herein with respect to IMD 16.

Figure 3:
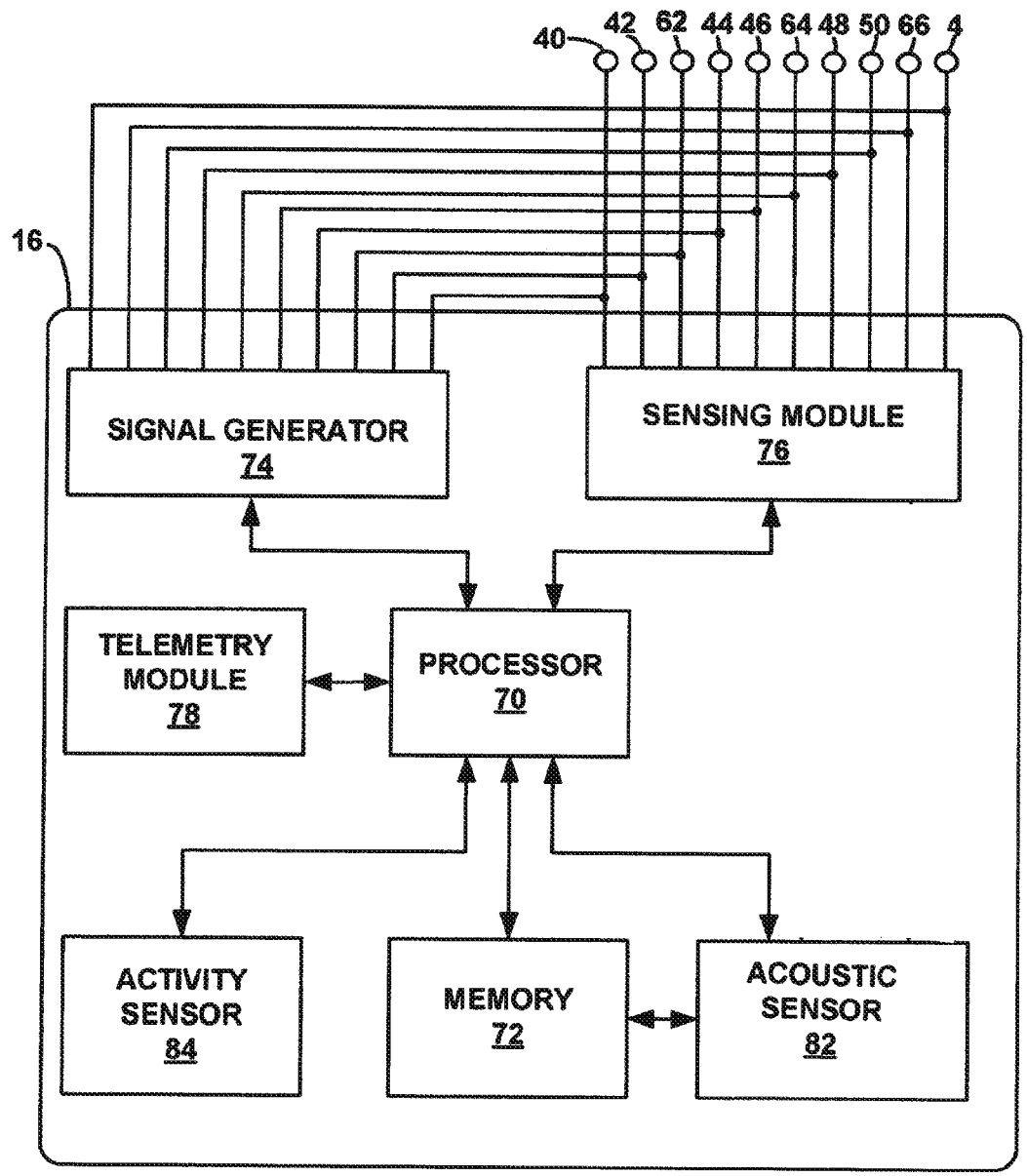
FIG. 3 is an exemplary functional block diagram of an exemplary configuration of the medical device of FIG. 1 according to an embodiment of the present disclosure.

FIG. 3 is a block diagram illustrating an example configuration of IMD 16. In the illustrated example, IMD 16 includes a processor 70, memory 72, signal generator 74, sensing module 76, telemetry module 78, acoustic sensor 82, and activity sensor 84. Memory 72 includes computer-readable instructions that, when executed by processor 70, cause IMD 16 and processor 70 to perform various functions attributed to IMD 16 and processor 70 herein. Memory 72 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Processor 70 may include any one or more of a microprocessor, a controller, a digital signal processor (DSP), an application specific integrated circuit (ASIC), a field-programmable gate array (FPGA), or equivalent discrete or analog logic circuitry. In some examples, processor 70 may include multiple components, such as any combination of one or more microprocessors, one or more controllers, one or more DSPs, one or more ASICs, or one or more FPGAs, as well as other discrete or integrated logic circuitry. The functions attributed to processor 70 herein may be embodied as software, firmware, hardware or any combination thereof. Generally, processor 70 controls signal generator 74 to deliver stimulation therapy to heart 12 of patient 14 according to a selected one or more of therapy programs or parameters, which may be stored in memory 72. As an example, processor 70 may control signal generator 74 to deliver electrical pulses with the amplitudes, pulse widths, frequency, or electrode polarities specified by the selected one or more therapy programs or parameters.

Signal generator 74 is configured to generate and deliver electrical stimulation therapy to patient 14. As shown in FIG. 3, signal generator 74 is electrically coupled to electrodes 4, 40, 42, 44, 46, 48, 50, 62, 64 and 66, e.g., via conductors of the respective leads 18, 20, and 22 and, in the case of housing electrode 4, within housing 8. For example, signal generator 74 may deliver pacing, defibrillation or cardioversion pulses to heart 12 via at least two of electrodes 4, 40, 42, 44, 46, 48, 50, 62, 64 and 66. In some examples, signal generator 74 delivers stimulation in the form of signals other than pulses such as sine waves, square waves, or other substantially continuous time signals.

Signal generator 74 may include a switch module (not shown) and processor 70 may use the switch module to select, e.g., via a data/address bus, which of the available electrodes are used to deliver the electrical stimulation. The switch module may include a switch array, switch matrix, multiplexer, or any other type of switching device suitable to selectively couple stimulation energy to selected electrodes. Electrical sensing module 76 monitors electrical cardiac signals from any combination of electrodes 4, 40, 42, 44, 46 48, 50, 62, 64, and 66. Sensing module 76 may also include a switch module which processor 70 controls to select which of the available electrodes are used to sense the heart activity, depending upon which electrode combination is used in the current sensing configuration.

Sensing module 76 may include one or more detection channels, each of which may comprise an amplifier. The detection channels may be used to sense the cardiac signals. Some detection channels may detect events, such as R-waves or P-waves, and provide indications of the occurrences of such events to processor 70. One or more other detection channels may provide the signals to an analog-to-digital converter, for conversion into a digital signal for processing or analysis by processor 70.

For example, sensing module 76 may comprise one or more narrow band channels, each of which may include a narrow band filtered sense-amplifier that compares the detected signal to a threshold. If the filtered and amplified signal is greater than the threshold, the narrow band channel indicates that a certain electrical cardiac event, e.g., depolarization, has occurred. Processor 70 then uses that detection in measuring frequencies of the sensed events.

In one example, at least one narrow band channel may include an R-wave or P-wave amplifier. In some examples, the R-wave and P-wave amplifiers may take the form of an automatic gain controlled amplifier that provides an adjustable sensing threshold as a function of the measured R-wave or P-wave amplitude. Examples of R-wave and P-wave amplifiers are described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety.

In some examples, sensing module 76 includes a wide band channel which may comprise an amplifier with a relatively wider pass band than the narrow band channels. Signals from the electrodes that are selected for coupling to the wide-band amplifier may be converted to multi-bit digital signals by an analog-to-digital converter (ADC) provided by, for example, sensing module 76 or processor 70. Processor 70 may analyze the digitized version of signals from the wide band channel. Processor 70 may employ digital signal analysis techniques to characterize the digitized signals from the wide band channel to, for example, detect and classify the patient's heart rhythm.

Processor 70 may detect and classify the patient's heart rhythm based on the cardiac electrical signals sensed by sensing module 76 employing any of the numerous signal processing methodologies known in the art. For example, processor 70 may maintain escape interval counters that may be reset upon sensing of R-waves by sensing module 76. The value of the count present in the escape interval counters when reset by sensed depolarizations may be used by processor 70 to measure the durations of R-R intervals, which are measurements that may be stored in memory 72. Processor 70 may use the count in the interval counters to detect a tachyarrhythmia, such as ventricular fibrillation or ventricular tachycardia. A portion of memory 72 may be configured as a plurality of recirculating buffers, capable of holding series of measured intervals, which may be analyzed by processor 70 to determine whether the patient's heart 12 is presently exhibiting atrial or ventricular tachyarrhythmia.

In some examples, processor 70 may determine that tachyarrhythmia has occurred by identification of shortened R-R interval lengths. Generally, processor 70 detects tachycardia when the interval length falls below 360 milliseconds (ms) and fibrillation when the interval length falls below 320 ms. These interval lengths are merely examples, and a user may define the interval lengths as desired, which may then be stored within memory 72. This interval length may need to be detected for a certain number of consecutive cycles, for a certain percentage of cycles within a running window, or a running average for a certain number of cardiac cycles, as examples.

In some examples, an arrhythmia detection method may include any suitable tachyarrhythmia detection algorithms. In one example, processor 70 may utilize all or a subset of the rule-based detection methods described in U.S. Pat. No. 5,545,186 to Olson et al., entitled, "PRIORITIZED RULE BASED METHOD AND APPARATUS FOR DIAGNOSIS AND TREATMENT OF ARRHYTHMIAS," which issued on Aug. 13, 1996, or in U.S. Pat. No. 5,755,736 to Gillberg et al., entitled, "PRIORITIZED RULE BASED METHOD AND APPARATUS FOR DIAGNOSIS AND TREATMENT OF ARRHYTHMIAS," which issued on May 26, 1998. U.S. Pat. No. 5,545,186 to Olson et al. and U.S. Pat. No. 5,755,736 to Gillberg et al. are incorporated herein by reference in their entireties. However, other arrhythmia detection methodologies may also be employed by processor 70 in some examples. For example, EGM morphology may be considered in addition to or instead of interval length for detecting tachyarrhythmias.

Generally, processor 70 detects a treatable tachyarrhythmia, such as VF, based on the EGM, e.g., the R-R intervals and/or morphology of the EGM, and selects a therapy to deliver to terminate the tachyarrhythmia, such as a defibrillation pulse of a specified magnitude. The detection of the tachyarrhythmia may include a number of phases or steps prior to delivery of the therapy, such as first phase, sometimes referred to as detection, in which a number of consecutive or proximate R-R intervals satisfies a first number of intervals to detect (NID) criterion, a second phase, sometimes referred to as confirmation, in which a number of consecutive or proximate R-R intervals satisfies a second, more restrictive NID criterion. Tachyarrhythmia detection may also include confirmation based on EGM morphology or other sensors subsequent to or during the second phase. Again, in some cases, processor 70 may mistakenly classify the patient's heart rhythm as a treatable tachyarrhythmia, e.g., as a result of a noisy EGM.

IMD 16 may also include one or more additional sensors, such as an acoustic sensor 82 and/or an activity sensor 84, for example. Acoustic sensor 82 generates an electrical signal based on sound or vibration, e.g., sensed heart sounds of patient 14, and may be implemented as a piezoelectric sensor, a microphone, an accelerometer, or other type of acoustical sensor. In some examples, acoustic sensor 82 may comprise more than one sensor. For example, acoustic sensor 82 may include multiple accelerometer devices. Activity sensor 84 may also comprise one or more accelerometers. Information obtained from acoustic sensor 82 and/or activity sensor 84 may be used to provide additional information, such as a risk assessment with regard to worsening heart failure or ventricular tachycardia and/or fibrillation.

In the illustrated example of FIG. 3, acoustic sensor 82 is enclosed within housing 8 of IMD 16. In some examples, acoustic sensor 82 may be formed integrally with an outer surface of housing 8. For example, acoustic sensor 82 may be a piezoelectric sensor attached to the outer surface of housing 8. In some examples, acoustic sensor 82 is located on a lead that is coupled to IMD 16 or may be implemented in a remote sensor that wirelessly communicates with IMD 16 via telemetry module 78. In any case, acoustic sensor 82 is electrically or wirelessly coupled to circuitry contained within housing 8 of IMD 16.

Activity sensor 84 may, for example, take the form of one or more accelerometers, or any other sensor known in the art for detecting activity, e.g., body movements or footfalls, or posture. In some examples, activity sensor 84 may comprise a three-axis accelerometer. In some examples, acoustic sensor 82 and activity sensor 84 may comprise one or more common accelerometers. Processor 70 may determine an activity level count at regular intervals based on the signal(s) from activity sensor 84. In some examples, processor 70 may determine a running average activity count based on the information provided by activity sensor 84. For example, the activity count may be calculated over a 1 second interval and the processor 70 may update the activity level count at a 1 second interval. A method of determining activity count from an accelerometer sensor is described in U.S. Pat. No. 6,449,508, to Sheldon et al, entitled, "ACCELEROMETER COUNT CALCULATION FOR ACTIVITY SIGNAL FOR AN IMPLANTABLE MEDICAL DEVICE," issued Sep. 10, 2002, and incorporated herein by reference in its entirety.

Activity sensor 84 may be located outside of the housing 8 of IMD 16. Activity sensor 84 may be located in such a manner to pick up chest motion, for example. Activity sensor 84 may be located on a lead that is coupled to IMD 16 or may be implemented in a remote sensor that wirelessly communicates with IMD 16 via telemetry module 78. In any case, activity sensor 84 is electrically or wirelessly coupled to circuitry contained within housing 8 of IMD 16.

Telemetry module 78 includes any suitable hardware, firmware, software or any combination thereof for communicating with another device, such as programmer 24 (FIG. 1). Under the control of processor 70, telemetry module 78 may receive downlink telemetry from and send uplink telemetry to programmer 24 with the aid of an antenna, which may be internal and/or external. In some examples, processor 70 may transmit cardiac signals, e.g., ECG or EGM signals, produced by sensing module 76 and/or signals by acoustic sensor 82 to programmer 24. Processor 70 may also generate and store marker codes indicative of different cardiac or other physiological events detected by sensing module 76 and transmit the marker codes to programmer 24. An example IMD with marker-channel capability is described in U.S. Pat. No. 4,374,382 to Markowitz, entitled, "MARKER CHANNEL TELEMETRY SYSTEM FOR A MEDICAL DEVICE," which issued on Feb. 15, 1983 and is incorporated herein by reference in its entirety. Information which processor 70 may transmit to programmer 24 via telemetry module 78 may also include an indication of a change in disease state of the heart, an indication of a change in heart response to the therapy provided or an indication that the heart continues to response in the same (or similar) manner to the therapy provided, the indications based on heart sounds and/or EGM signals. Such information may be included as part of a marker channel with an EGM.

Figure 4:
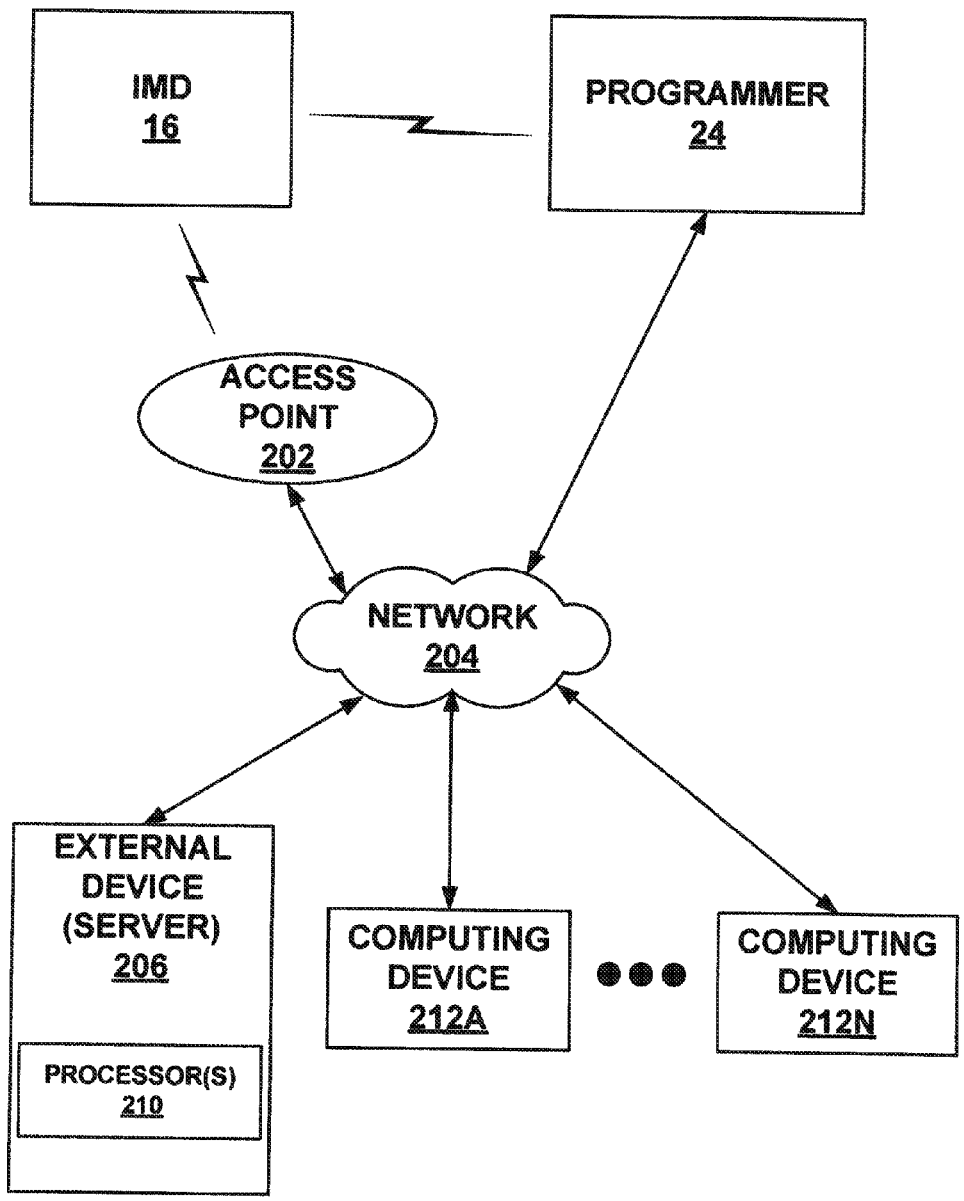
FIG. 4 is an exemplary block diagram illustrating an example system that includes an external device, such as a server, and one or more computing devices coupled to the medical device and programmer shown in FIG. 1 via a network.

FIG. 4 is an exemplary block diagram illustrating an example system that includes an external device, such as a server 206, and one or more computing devices 212A-212N that are coupled to the IMD 16 and programmer 24 shown in FIG. 1 via a network 204. Network 204 may be generally used to transmit diagnostic information (e.g., activity level and/or heart sounds) from an IMD 16 to a remote external computing device. In some examples, the acoustic and/or EGM signals may be transmitted to an external device for processing.

In some examples, the information transmitted by IMD 16 may allow a clinician or other healthcare professional to monitor patient 14 remotely. In some examples, IMD 16 may use its telemetry module 78 to communicate with programmer 24 via a first wireless connection, and to communicate with an access point 202 via a second wireless connection, e.g., at different times. In the example of FIG. 4, access point 202, programmer 24, server 206, and computing devices 212A-212N are interconnected, and able to communicate with each other, through network 204. In some cases, one or more of access point 202, programmer 24, server 206, and computing devices 212A-3212N may be coupled to network 204 via one or more wireless connections. IMD 16, programmer 24, server 206, and computing devices 212A-212N may each comprise one or more processors, such as one or more microprocessors, DSPs, ASICs, FPGAs, programmable logic circuitry, or the like, that may perform various functions and operations, such as those described herein.

Access point 202 may comprise a device that connects to network 204 via any of a variety of connections, such as telephone dial-up, digital subscriber line (DSL), or cable modem connections. In other examples, access point 202 may be coupled to network 204 through different forms of connections, including wired or wireless connections. In some examples, access point 202 may be co-located with patient 14 and may comprise one or more programming units and/or computing devices (e.g., one or more monitoring units) that may perform various functions and operations described herein. For example, access point 202 may include a home-monitoring unit that is co-located with patient 14 and that may monitor the activity of IMD 16. In some examples, server 206 or computing devices 212 may control or perform any of the various functions or operations described herein, e.g., determine, based on the sensed cardiac signal, whether homeostasis variations, such as hypokalemia, are occurring, as described below in detail.

In some cases, server 206 may be configured to provide a secure storage site for archival of diagnostic information (e.g., attendant circumstances such as patient posture, activity level, or heart sounds) that has been collected and generated from IMD 16 and/or programmer 24. Network 204 may comprise a local area network, wide area network, or global network, such as the Internet. In some cases, programmer 24 or server 206 may assemble homeostasis variations information in web pages or other documents for viewing by trained professionals, such as clinicians, via viewing terminals associated with computing devices 212. The system of FIG. 4 may be implemented, in some aspects, with general network technology and functionality similar to that provided by the Medtronic CareLink® Network developed by Medtronic, Inc., of Minneapolis, Minn.

Figure 5:
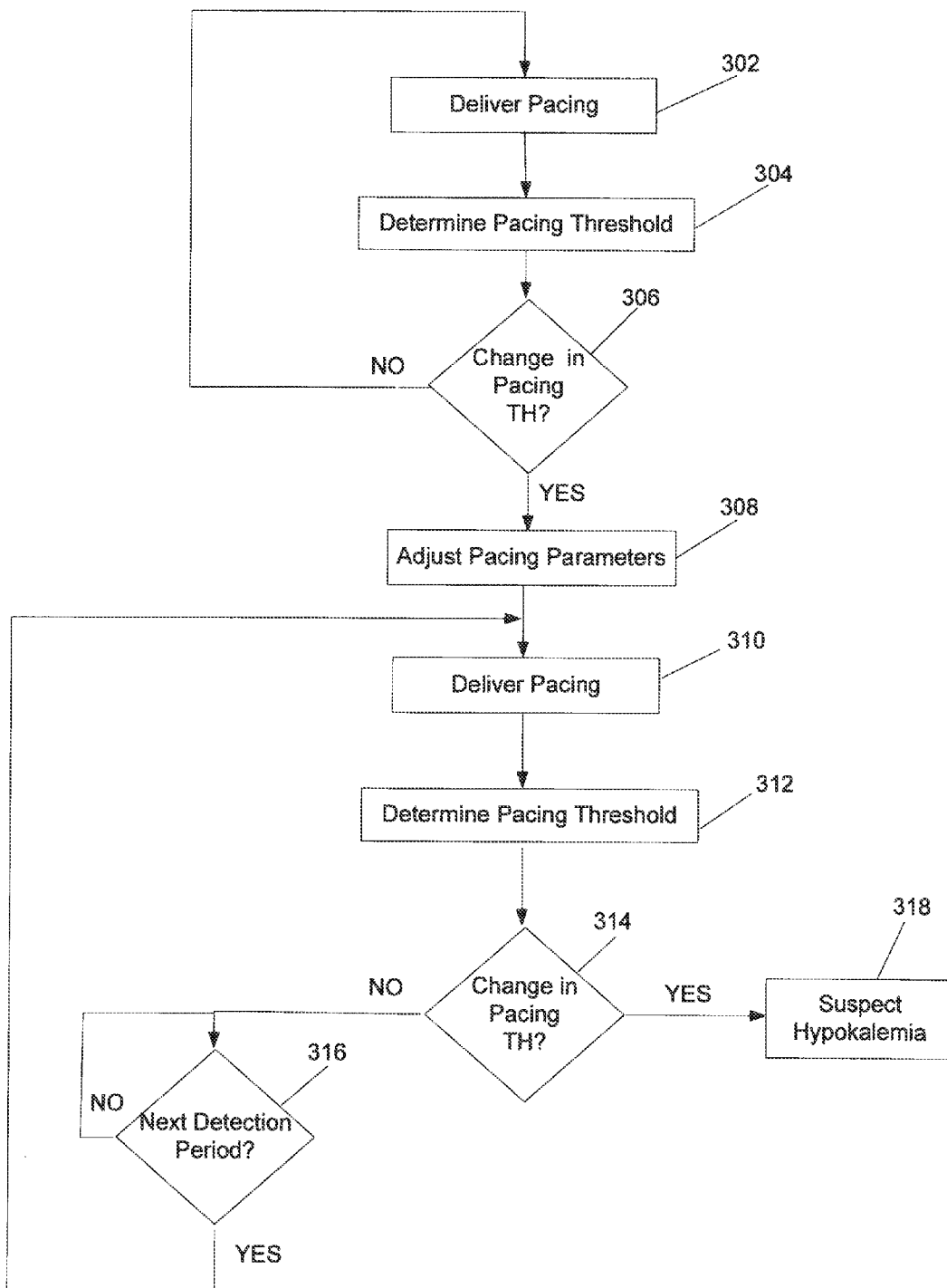
FIG. 5 is a flow chart of an exemplary method for monitoring cardiac function in a medical device according to an embodiment of the present disclosure.

FIG. 5 is a flowchart of an exemplary method for monitoring cardiac function in a medical device according to an embodiment of the present disclosure. During delivery of pacing therapy, processor 70 determines a minimum voltage associated with the delivered therapy that is capable of evoking a heartbeat, commonly referred to as a pacing threshold. According to one embodiment of the present disclosure, pacing therapy is delivered, the associated pacing threshold is determined, the current determined pacing threshold is compared to a prior determined pacing threshold, and the detection of homeostasis variations as described herein is initiated in response to the comparison. For example, once the current pacing threshold is determined to be greater than the previous pacing threshold, indicating an increase in the pacing threshold, processor 70 initiates a homeostasis variations detection mode for detection of homeostasis variations.

According to another embodiment, processor 70 may initiate a homeostasis variations detection mode for detection of homeostasis variations once the current pacing threshold is determined to be less than the previous pacing threshold, indicating a decrease in the pacing threshold. In yet another embodiment, processor 70 may initiate a homeostasis variations detection mode for detection of homeostasis variations once either the current pacing threshold is determined to be greater than the previous pacing threshold, indicating an increase in the pacing threshold, or the current pacing threshold is determined to be less than the previous pacing threshold, indicating a decrease in the pacing threshold. When in the homeostasis variation mode, the device adjusts delivery of the pacing therapy and checks for changes in the pacing threshold in response to delivery of the adjusted pacing therapy. In one exemplary embodiment, when in the homeostasis variations detection mode, the device adjusts the pulse width and the rate at which the pacing therapy is delivered, i.e., number of times per day. Based on the determined changes or lack thereof, the device determines that either hypokalemia is suspected, i.e., when the pacing threshold increases, or hyperkalemia is suspected, i.e., when the pacing threshold decreases, and adjusts operation of the device accordingly, as described in detail below.

Therefore, as illustrated in FIG. 5, according to an embodiment of the present disclosure, during normal delivery of pacing therapy, i.e., when the device is not in the homeostasis variations detection mode, the device delivers pacing therapy using normal device programmed pacing parameters, Block 302. Once the pacing therapy is delivered, the device determines a current pacing therapy threshold, Block 304, and based on the current pacing therapy threshold, determines whether there has been a change in the pacing threshold, Block 306. According to one embodiment, during normal delivery, pacing therapy is delivered in Block 302 using a 0.5 millisecond pulse width, for example, and the device determines the current pacing therapy threshold in Block 304 at a rate of once per day, such as during the evening when the patient is assumed to be asleep. It is understood that the pacing parameters may be initially programmed at parameters other than the specific example of 0.5 ms, depending upon the specific capabilities of the device, and therefore any device programmed parameters are contemplated by the present disclosure.

In order to determine whether changes in the pacing threshold are occurring in Block 306, the device determines whether there is an increase in the pacing threshold by comparing the current determined pacing therapy threshold to a prior determined pacing threshold. If the pacing threshold has not increased, i.e., the current pacing threshold is not greater than the previous determined pacing threshold, No in Block 306, the device waits until the next scheduled determination of the pacing threshold. If a change in the pacing threshold is determined, Yes in Block 306, the device advances to a homeostasis variations detection mode for detection of homeostasis variations.

When in the homeostasis variations detection mode, Blocks 308-316, the device adjusts delivery of the pacing therapy, Block 308, delivers the adjusted pacing therapy, Block 310, and determines a pacing threshold associated with delivery of the adjusted pacing therapy, Block 312. During adjusting of the pacing therapy the device alters one or more of the pacing parameters, such as the pulse width and the rate at which the pacing therapy is delivered, for example. According to one exemplary embodiment, the device changes the pulse width and rate of delivery from the 0.5 millisecond delivered once per day, utilized during normal pacing delivery, Blocks 302-306, to a pulse width of 0.06 milliseconds every hour. Once the pacing threshold associated with delivery of the adjusted pacing therapy is determined, the device determines whether there has been a change in the pacing threshold in response to delivery of the adjusted pacing therapy, Block 314.

In particular, according to one embodiment of the present disclosure, while in the homeostasis variation detection mode, the device determines whether there has been a predetermined increase in the pacing threshold during delivery of the adjusted pacing therapy. For example, given the adjusted pacing therapy is delivered having a 0.06 ms pulse width, the device determines whether there is a change in pacing threshold between a current determined pacing threshold and a previous determined pacing threshold at the same adjusted pulse width setting, i.e., 0.06 ms. If an increase in the pacing threshold is not determined to occur during delivery of the adjusted therapy and therefore there is not a change in the pacing threshold, NO in Block 314, the device waits until the next detection period for determining the pacing threshold, i.e., one hour, Block 316. Once it is determined that the next detection period is identified, YES in Block 316, the adjusted pacing therapy is delivered Block 310, and the process is repeated. According to one embodiment, the device determines that an increase in the pacing threshold occurs if there is a one-step increase in the current adjusted pacing threshold from a prior adjusted pacing threshold determination. According to one embodiment, a one-step increase in the pacing threshold corresponds to an increase of approximately one tenth of a volt, so that, for example, an increase from 0.1 volts to 0.2 volts would correspond to a one-step increase.

Other changes in parameter can be utilized in Block 308. For example, according to another exemplary embodiment, the device changes a single parameter of the pacing therapy, such as the pulse width, from the 0.5 millisecond delivered once per day, utilized during normal pacing delivery, Blocks 302-306, to a pacing therapy having a pulse width of 0.06 milliseconds and delivered once per day, and so forth.

Once it is determined that the pacing threshold has increased and therefore a change in the pacing threshold between a current and a previous measurement at the adjusted pulse width has occurred, YES in Block 314, the device determines that hypokalemia is likely present, Block 318, and an alert may be generated and/or the determination of hypokalemia likely being present is stored either remotely or within the device. The device may then verify the likelihood of the presence of hypokalemia using secondary parameters, such as changes in ECG, electrograms, changes in impedance, or changes in heart sounds, etc. If the presence of hypokalemia is verified using one or more of the secondary parameters, an alert may also be generated to alert the patient and/or the physician.

Figure 6:
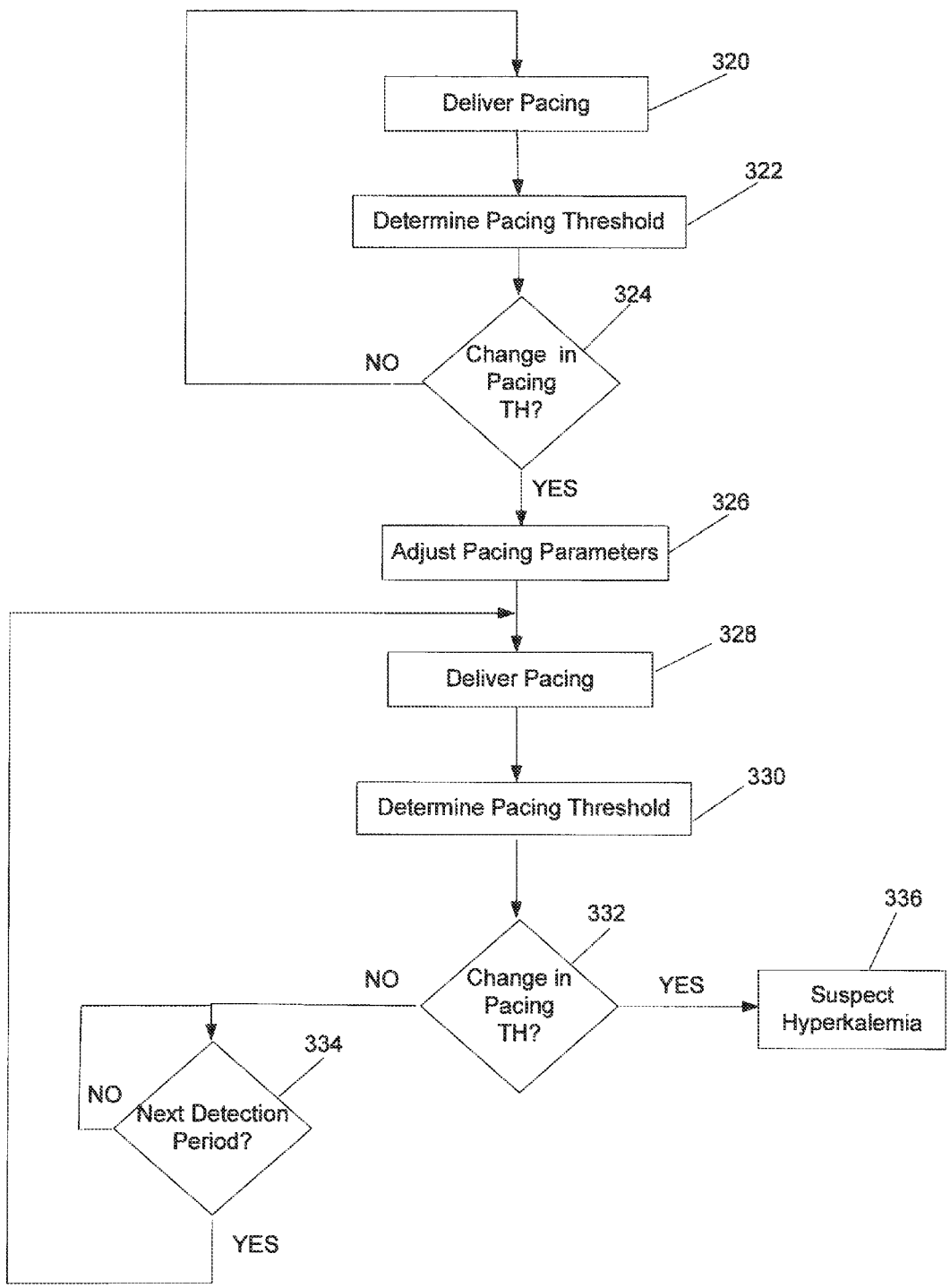
FIG. 6 is a flowchart of an exemplary method for monitoring cardiac function in a medical device according to an embodiment of the present disclosure.

FIG. 6 is a flowchart of an exemplary method for monitoring cardiac function in a medical device according to an embodiment of the present disclosure. As illustrated in FIG. 6, during normal delivery of pacing therapy, i.e., when the device is not in the homeostasis variations detection mode, the device delivers pacing therapy using normal device programmed pacing parameters, Block 320. Once the pacing therapy is delivered, the device determines a current pacing therapy threshold, Block 322, and based on the current pacing therapy threshold, determines whether there has been a change in the pacing threshold, Block 324. According to one embodiment, during normal delivery, pacing therapy is delivered in Block 302 using a 0.5 millisecond pulse width, for example, and the device determines the current pacing therapy threshold in Block 304 at a rate of once per day, such as during the evening when the patient is assumed to be asleep. It is understood that the pacing parameters may be initially programmed at parameters other than the specific example of 0.5 ms, depending upon the specific capabilities of the device, and therefore any device programmed parameters are contemplated by the present disclosure.

In order to determine whether changes in the pacing threshold are occurring in Block 324, the device determines whether there is a decrease in the pacing threshold by comparing the current determined pacing therapy threshold to a prior determined pacing threshold. If the pacing threshold has not decreased, i.e., the current pacing threshold is not less than the previous determined pacing threshold, No in Block 324, the device waits until the next scheduled determination of the pacing threshold. If a change in the pacing threshold is determined, Yes in Block 324, the device advances to a homeostasis variations detection mode for detection of homeostasis variations.

When in the homeostasis variations detection mode, Blocks 326-336, the device adjusts delivery of the pacing therapy, Block 326, delivers the adjusted pacing therapy, Block 328, and determines a pacing threshold associated with delivery of the adjusted pacing therapy, Block 330. During adjusting of the pacing therapy the device alters one or more of the pacing parameters, such as the pulse width and the rate at which the pacing therapy is delivered, for example. According to one exemplary embodiment, the device changes the pulse width and rate of delivery from the 0.5 millisecond delivered once per day, utilized during normal pacing delivery, Blocks 320-324, to a pulse width of 0.06 milliseconds every hour. Once the pacing threshold associated with delivery of the adjusted pacing therapy is determined, the device determines whether there has been a change in the pacing threshold in response to delivery of the adjusted pacing therapy, Block 332.

In particular, according to one embodiment of the present disclosure, while in the homeostasis variation detection mode, the device determines whether there has been a predetermined decrease in the pacing threshold during delivery of the adjusted pacing therapy. For example, given the adjusted pacing therapy is delivered having a 0.06 ms pulse width, the device determines whether there is a change in pacing threshold between a current determined pacing threshold and a previous determined pacing threshold at the same adjusted pulse width setting, i.e., 0.06 ms. If a decrease in the pacing threshold is not determined to occur during delivery of the adjusted therapy and therefore there is not a change in the pacing threshold, NO in Block 332, the device waits until the next detection period for determining the pacing threshold, i.e., one hour, Block 334. Once it is determined that the next detection period is identified, YES in Block 334, the adjusted pacing therapy is delivered Block 328, and the process is repeated. According to one embodiment, the device determines that a decrease in the pacing threshold occurs if there is a one-step increase in the current adjusted pacing threshold from a prior adjusted pacing threshold determination. According to one embodiment, a one-step decrease in the pacing threshold corresponds to a decrease of approximately one tenth of a volt, so that, for example, a decrease from 0.1 volts to 0.2 volts would correspond to a one-step decrease.

Other changes in parameter can be utilized in Block 326. For example, according to another exemplary embodiment, the device changes a single parameter of the pacing therapy, such as the pulse width, from the 0.5 millisecond delivered once per day, utilized during normal pacing delivery, Blocks 320-324, to a pacing therapy having a pulse width of 0.06 milliseconds and delivered once per day, and so forth.

Once it is determined that the pacing threshold has decreased and therefore a change in the pacing threshold between a current and a previous measurement at the adjusted pulse width has occurred, YES in Block 332, the device determines that hyperkalemia is likely present, Block 336, and an alert may be generated and/or the determination of hyperkalemia likely being present is stored either remotely or within the device. The device may then verify the likelihood of the presence of hyperkalemia using secondary parameters, such as changes in ECG, changes in electrograms, changes in impedance, or changes in heart sounds, etc. If the presence of hyperkalemia is verified using one or more of the secondary parameters, an alert may also be generated to alert the patient and/or the physician.

Figure 7:
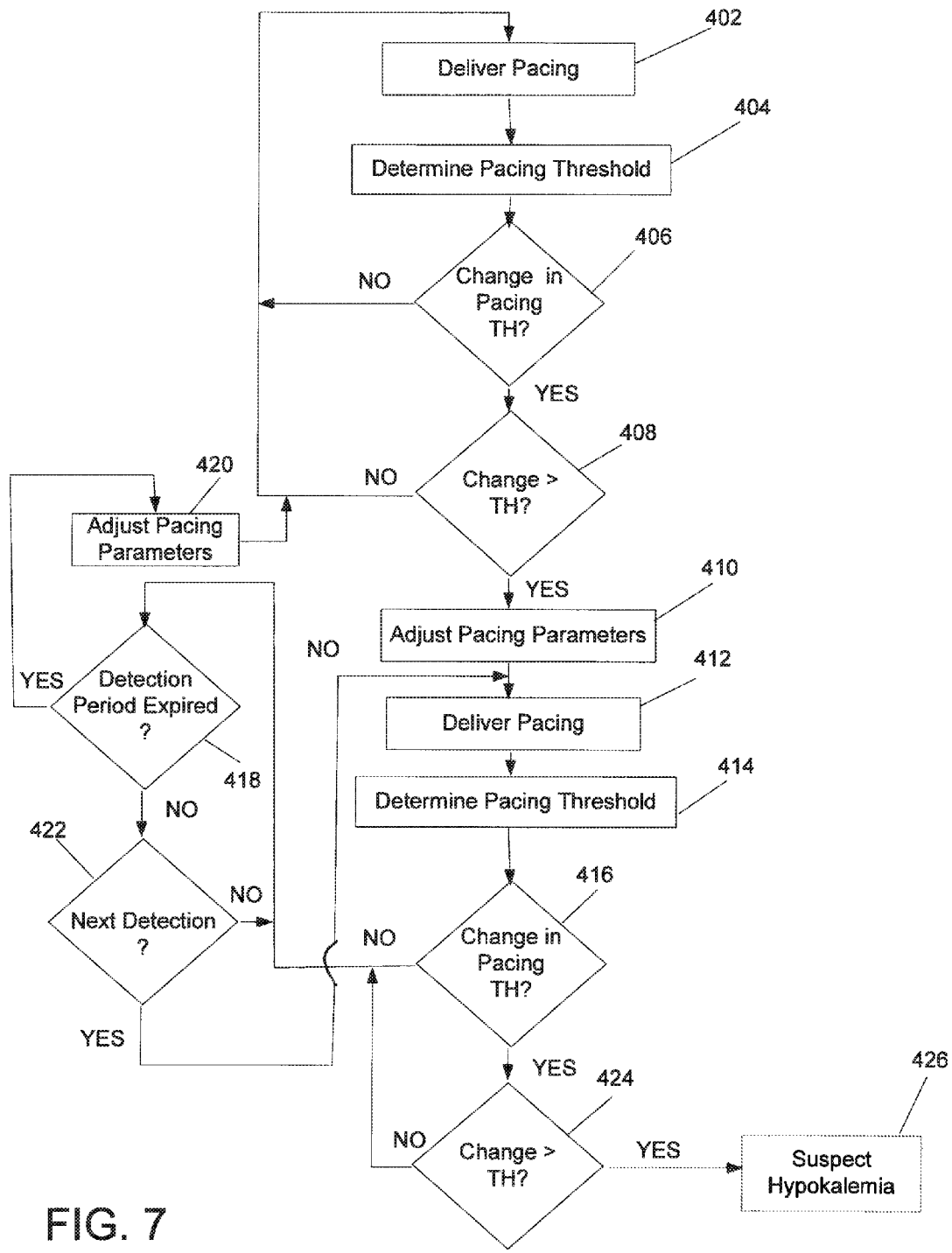
FIG. 7 is a flowchart of an exemplary method for monitoring cardiac function in a medical device according to an embodiment of the present disclosure.

FIG. 7 is a flowchart of an exemplary method for monitoring cardiac function in a medical device according to an embodiment of the present disclosure. As illustrated in FIG. 7, during normal delivery of pacing therapy by the device, i.e., when the device is not in the homeostasis variations detection mode, the device delivers pacing therapy using normal device programmed pacing parameters, Block 402. Once the pacing therapy is delivered, the device determines a current pacing therapy threshold, Block 404, and based on the current pacing therapy threshold, determines whether there has been a change in the pacing threshold, Block 406. Using the exemplary embodiment described above, during normal delivery, pacing therapy is delivered in Block 402 using a 0.5 millisecond pulse width, for example, and the device determines the current pacing therapy threshold in Block 404 at a rate of once per day, such as during the evening when the patient is assumed to be asleep. In order to determine whether changes in the pacing threshold are occurring in Block 406, the device determines whether there is an increase in the pacing threshold by comparing the current determined pacing therapy threshold to a prior determined pacing threshold associated with parameters of the current delivered pacing therapy, Block 402. If the pacing threshold has not increased, i.e., the current pacing threshold is not greater than the prior determined pacing threshold, NO in Block 406, the device waits until the next scheduled determination of the pacing threshold (i.e., once per day for example) and the pacing threshold determination process is repeated. If a change in the pacing threshold is determined, YES in Block 406, the device determines whether the pacing threshold change is greater than a change threshold, Block 408, associated with parameters of the current delivered pacing therapy, Block 402.

According to an exemplary embodiment of the present disclosure, when not in the homeostasis mode, in order to determine whether the pacing threshold change is greater than a change threshold, Block 408, the device determines whether there is a one-step or greater change in the current determined pacing threshold from the previously determined pacing threshold. If the change in pacing threshold is not greater than a one-step change, NO in Block 408, the device waits until the next scheduled determination of the pacing threshold (once per day, for example), and the pacing threshold determination process is repeated. If the change in pacing threshold is greater than the pacing threshold change threshold, YES in Block 408, the device advances to the homeostasis variations detection mode during which the device detects for the presence of homeostasis variations in the patient.

As described above, when in the homeostasis variations detection mode, Blocks 410-426, the device adjusts delivery of the pacing therapy, Block 410, delivers the adjusted pacing therapy, Block 412, and determines a pacing threshold associated with delivery of the adjusted pacing therapy, Block 414. During adjusting of the pacing therapy the device alters one or more of the pacing parameters, such as the pulse width and the rate at which the pacing therapy is delivered, for example. According to one exemplary embodiment, the device changes the pulse width and rate of delivery from the 0.5 millisecond delivered once per day, utilized during normal pacing delivery, Blocks 402-408, to a pulse width of 0.06 milliseconds and delivered every 15 minutes for one hour. Each time the pacing threshold associated with delivery of the adjusted pacing therapy is determined, Block 414, the device determines whether there has been a change in the pacing threshold in response to delivery of the adjusted pacing therapy, Block 416.

In particular, according to one embodiment of the present disclosure, while in the homeostasis variation detection mode, in order to determine whether there has been a change in the pacing threshold in response to delivery of the adjusted pacing therapy, Block 416, the device determines whether there has been a predetermined increase in the pacing threshold when pacing therapy is delivered at the adjusted pulse width, i.e., 0.6 ms, compared to a previous measurement at the adjusted pulse width. If an increase in the pacing threshold is not determined to occur during delivery of the adjusted therapy and therefore there is not a change in the pacing threshold, NO in Block 416, the device determines whether the detection period, i.e., one hour, has expired Block 418. If the detection period has expired, YES in Block 418, the device transitions from the homeostasis detection mode, Blocks 410-426, back to the normal pacing therapy mode Blocks 402-408, adjusting the pacing parameters, Block 420, back to those previous utilized during normal pacing therapy, Blocks 402-408.

If the detection period has not expired, NO in Block 418, the device waits until the next detection period for determining the pacing threshold, i.e., 15 minutes, Block 422. Once it is determined that the next detection period is set to occur, YES in Block 422, the process is repeated with the adjusted pacing therapy being delivered, Block 412, and a determination being made as to whether changes in the pacing threshold associated with the delivered therapy occur, Blocks 414 and 416.

Once a change in the pacing threshold is determined to have occurred, YES in Block 416, the device determines whether the pacing threshold change is greater than a change threshold, Block 424, associated with the adjusted pacing parameters, Block 410. According to an exemplary embodiment of the present disclosure, while in the homeostasis mode, in order to determine whether the adjusted pacing threshold change is greater than a change threshold, Block 424, the device determines whether there is a four-step or greater change in the current determined pacing threshold from the previously determined pacing threshold. If the change in pacing threshold between a current pacing threshold and a previous pacing threshold determined at the adjusted pulse width, i.e., 0.6 ms, is not greater than the change threshold, NO in Block 424, the device determines whether the detection period, i.e., one hour, has expired Block 418, If the detection period has expired, YES in Block 418, the device transitions from the homeostasis detection mode, Blocks 410-426, back to the normal pacing therapy mode Blocks 402-408, adjusting the pacing parameters, Block 420, back to those previously utilized during normal pacing therapy, Blocks 402-408. If the detection period has not expired, NO in Block 418, the device waits until the next detection period for determining the pacing threshold, and the process is repeated as described above.

Once it is determined that the change in pacing threshold is greater than the change threshold, YES in Block 424, the device determines that hypokalemia is likely present, Block 426, and an alert may be generated and/or the determination of hypokalemia likely being present is stored either remotely or within the device. The device may also verify the likelihood of the presence of hypokalemia using secondary parameters, such as changes in ECG, electrograms, changes in impedance, or changes in heart sounds, etc. If the presence of hypokalemia is verified using one or more of the secondary parameters, an alert may also be generated to alert the patient and/or the physician or the information may be stored.

Figure 8:
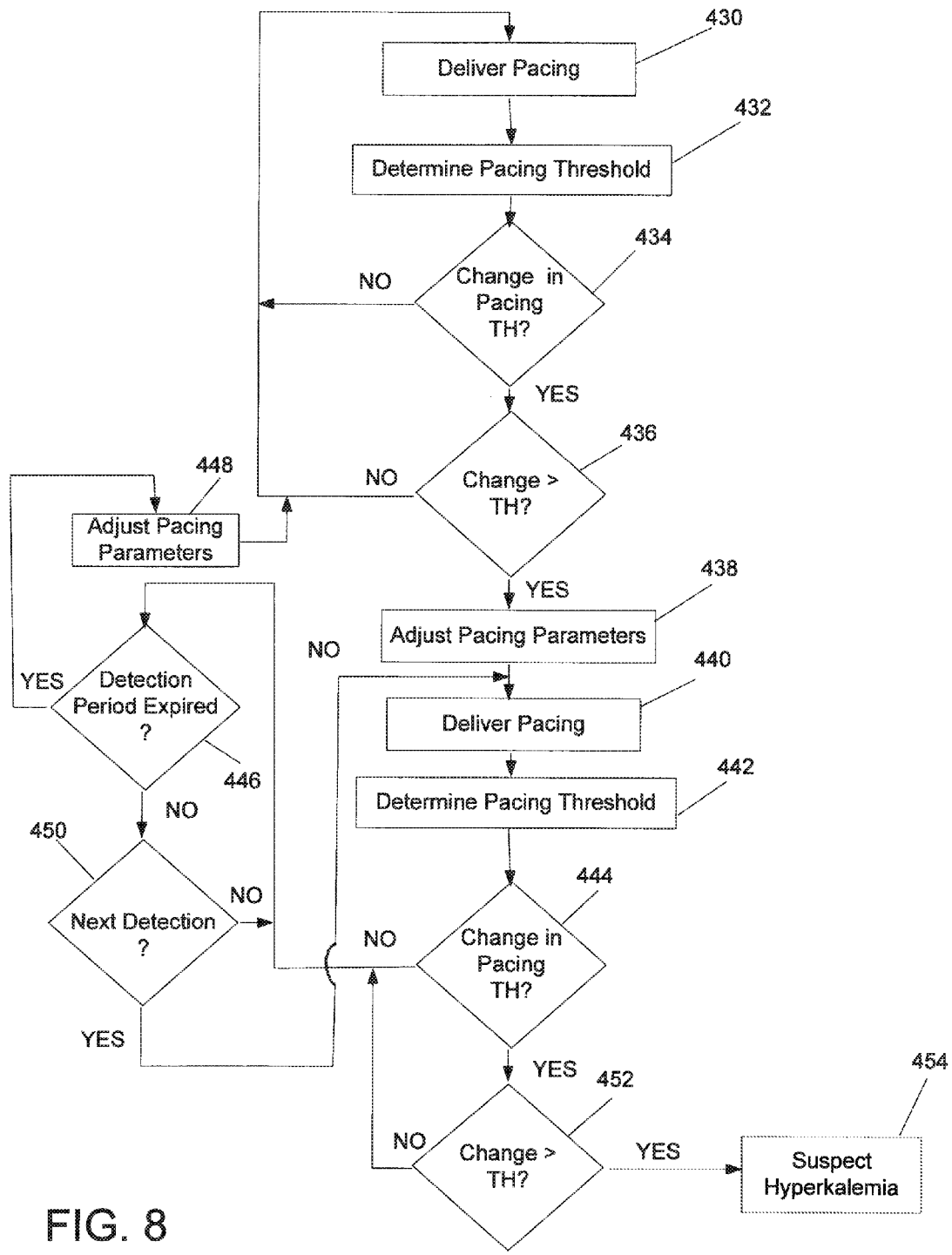
FIG. 8 is a flowchart of an exemplary method for monitoring cardiac function in a medical device according to an embodiment of the present disclosure.

FIG. 8 is a flowchart of an exemplary method for monitoring cardiac function in a medical device according to an embodiment of the present disclosure. As illustrated in FIG. 8, during normal delivery of pacing therapy by the device, i.e., when the device is not in the homeostasis variations detection mode, the device delivers pacing therapy using normal device programmed pacing parameters, Block 430. Once the pacing therapy is delivered, the device determines a current pacing therapy threshold, Block 432, and based on the current pacing therapy threshold, determines whether there has been a change in the pacing threshold, Block 434. Using the exemplary embodiment described above, during normal delivery, pacing therapy is delivered in Block 430 using a 0.5 millisecond pulse width, for example, and the device determines the current pacing therapy threshold in Block 432 at a rate of once per day, such as during the evening when the patient is assumed to be asleep. In order to determine whether changes in the pacing threshold are occurring in Block 434, the device determines whether there is a decrease in the pacing threshold by comparing the current determined pacing threshold to a prior determined pacing threshold associated with parameters of the current delivered pacing therapy, Block 430. If the pacing threshold has not decreased, i.e., the current pacing threshold is not less than the prior determined pacing threshold, NO in Block 434, the device waits until the next scheduled determination of the pacing threshold (i.e., once per day for example) and the pacing threshold determination process is repeated. If a change in the pacing threshold is determined, YES in Block 434, the device determines whether the pacing threshold change is greater than a change threshold, Block 436, associated with parameters of the current delivered pacing therapy, Block 430.

According to an exemplary embodiment of the present disclosure, when not in the homeostasis mode, in order to determine whether the pacing threshold change is greater than a change threshold, Block 436, the device determines whether there is a one-step or greater change in the current determined pacing threshold from the previously determined pacing threshold. If the change in pacing threshold is not greater than a one-step change, NO in Block 436, the device waits until the next scheduled determination of the pacing threshold (once per day, for example), and the pacing threshold determination process is repeated. If the change in pacing threshold is greater than the pacing threshold change threshold, YES in Block 436, the device advances to the homeostasis variations detection mode during which the device detects for the presence of homeostasis variations in the patient.

As described above, when in the homeostasis variations detection mode, Blocks 438-454, the device adjusts delivery of the pacing therapy, Block 438, delivers the adjusted pacing therapy, Block 440, and determines a pacing threshold associated with delivery of the adjusted pacing therapy, Block 442. During adjusting of the pacing therapy the device alters one or more of the pacing parameters, such as the pulse width and the rate at which the pacing therapy is delivered, for example. According to one exemplary embodiment, the device changes the pulse width and rate of delivery from the 0.5 millisecond delivered once per day, utilized during normal pacing delivery, Blocks 430-436, to a pulse width of 0.06 milliseconds and delivered every 15 minutes for one hour. Each time the pacing threshold associated with delivery of the adjusted pacing therapy is determined, Block 442, the device determines whether there has been a change in the pacing threshold in response to delivery of the adjusted pacing therapy, Block 444.

In particular, according to one embodiment of the present disclosure, while in the homeostasis variation detection mode, in order to determine whether there has been a change in the pacing threshold in response to delivery of the adjusted pacing therapy, Block 444, the device determines whether there has been a predetermined decrease in the pacing threshold when pacing therapy is delivered at the adjusted pulse width, i.e., 0.6 ms, compared to a previous measurement at the adjusted pulse width. If a decrease in the pacing threshold is not determined to occur during delivery of the adjusted therapy and therefore there is not a change in the pacing threshold, NO in Block 444, the device determines whether the detection period, i.e., one hour, has expired Block 446. If the detection period has expired, YES in Block 446, the device transitions from the homeostasis detection mode, Blocks 438-454, back to the normal pacing therapy mode Blocks 430-436, adjusting the pacing parameters, Block 448, back to those previous utilized during normal pacing therapy, Blocks 430-436.

If the detection period has not expired, No in Block 4446, the device waits until the next detection period for determining the pacing threshold, i.e., 15 minutes, Block 4450. Once it is determined that the next detection period is set to occur, YES in Block 450, the process is repeated with the adjusted pacing therapy being delivered, Block 440, and a determination being made as to whether changes in the pacing threshold associated with the delivered therapy occur, Blocks 442 and 444.

Once a change in the pacing threshold is determined to have occurred, Yes in Block 444, the device determines whether the pacing threshold change is greater than a change threshold, Block 452, associated with the adjusted pacing parameters, Block 438. According to an exemplary embodiment of the present disclosure, while in the homeostasis mode, in order to determine whether the adjusted pacing threshold change is greater than a change threshold, Block 452, the device determines whether there is a four-step or greater change in the current determined pacing threshold from the previously determined pacing threshold. If the change in pacing threshold between a current pacing threshold and a previous pacing threshold determined at the adjusted pulse width, i.e., 0.6 ms, is not greater than the change threshold, NO in Block 452, the device determines whether the detection period, i.e., one hour, has expired Block 446, If the detection period has expired, YES in Block 446, the device transitions from the homeostasis detection mode, Blocks 438-454, back to the normal pacing therapy mode Blocks 430-436, adjusting the pacing parameters, Block 448, back to those previously utilized during normal pacing therapy, Blocks 430-436. If the detection period has not expired, No in Block 446, the device waits until the next detection period for determining the pacing threshold, and the process is repeated as described above.

Once it is determined that the change in pacing threshold is greater than the change threshold, YES in Block 452, the device determines that hyperkalemia is likely present, Block 454, and an alert may be generated and/or the determination of hyperkalemia likely being present is stored either remotely or within the device. The device may also verify the likelihood of the presence of hyperkalemia using secondary parameters, such as changes in ECG, changes in electrograms, changes in impedance, or changes in heart sounds, etc. If the presence of hyperkalemia is verified using one or more of the secondary parameters, an alert may also be generated to alert the patient and/or the physician or the information may be stored.

Figure 9:
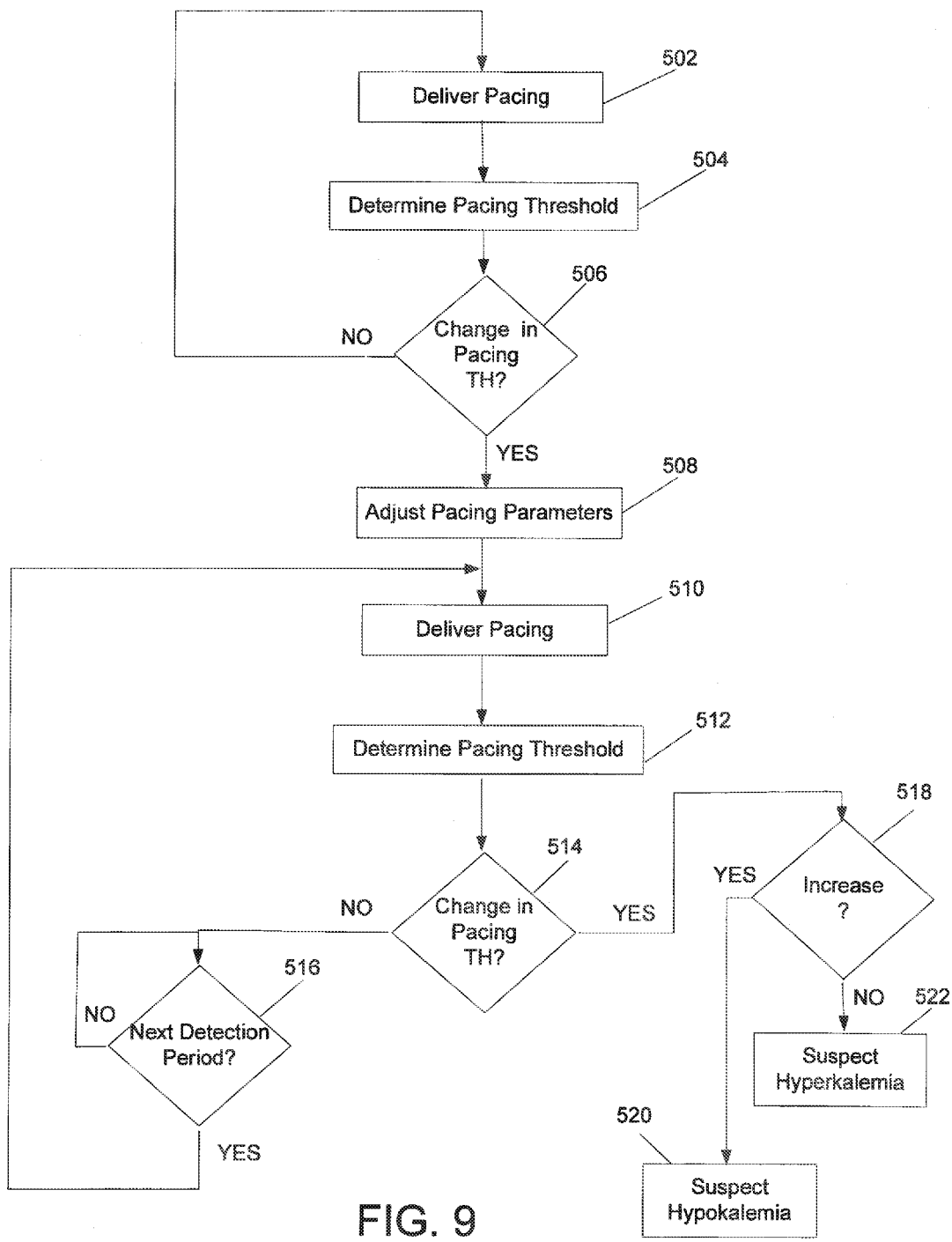
FIG. 9 is a flowchart of an exemplary method for monitoring cardiac function in a medical device according to an embodiment of the present disclosure.

FIG. 9 is a flowchart of an exemplary method for monitoring cardiac function in a medical device according to an embodiment of the present disclosure. As illustrated in FIG. 9, according to an embodiment of the present disclosure, during normal delivery of pacing therapy, i.e., when the device is not in the homeostasis variations detection mode, the device delivers pacing therapy using normal device programmed pacing parameters, Block 502. Once the pacing therapy is delivered, the device determines a current pacing therapy threshold, Block 504, and based on the current pacing therapy threshold, determines whether there has been a change in the pacing threshold, Block 506. According to one embodiment, during normal delivery, pacing therapy is delivered in Block 502 using a 0.5 millisecond pulse width, for example, and the device determines the current pacing therapy threshold in Block 504 at a rate of once per day, such as during the evening when the patient is assumed to be asleep. It is understood that the pacing parameters may be initially programmed at parameters other than the specific example of 0.5 ms, depending upon the specific capabilities of the device, and therefore any device programmed parameters are contemplated by the present disclosure.

In order to determine whether changes in the pacing threshold are occurring in Block 506, the device determines whether there is either an increase in the pacing threshold or a decrease in the pacing threshold by comparing the current determined pacing therapy threshold to a prior determined pacing threshold. If the pacing threshold has neither increased nor decreased, i.e., the current pacing threshold is neither greater than nor less than the previous determined pacing threshold, NO in Block 506, the device waits until the next scheduled determination of the pacing threshold. Once either the current pacing threshold is determined to be greater than the previous pacing threshold, indicating an increase in the pacing threshold, or the current pacing threshold is determined to be less than the previous pacing threshold, indicating a decrease in the pacing threshold, a change in the pacing threshold is determined to occur, YES in Block 506, and the device advances to a homeostasis variations detection mode for detection of homeostasis variations.

When in the homeostasis variations detection mode, Blocks 508-522, the device adjusts delivery of the pacing therapy, Block 508, delivers the adjusted pacing therapy, Block 510, and determines a pacing threshold associated with delivery of the adjusted pacing therapy, Block 512. During adjusting of the pacing therapy the device alters one or more of the pacing parameters, such as the pulse width and the rate at which the pacing therapy is delivered, for example. According to one exemplary embodiment, the device changes the pulse width and rate of delivery from the 0.5 millisecond delivered once per day, utilized during normal pacing delivery, Blocks 502-506, to a pulse width of 0.06 milliseconds every hour. Once the pacing threshold associated with delivery of the adjusted pacing therapy is determined, the device determines whether there has been a change in the pacing threshold in response to delivery of the adjusted pacing therapy, Block 514.

In particular, according to one embodiment of the present disclosure, while in the homeostasis variation detection mode, the device determines whether there has been either a predetermined increase in the pacing threshold during delivery of the adjusted pacing therapy, or a predetermined decrease in the pacing threshold during delivery of the adjusted pacing therapy. For example, given the adjusted pacing therapy is delivered having a 0.06 ms pulse width, the device determines whether there is a change in pacing threshold between a current determined pacing threshold and a previous determined pacing threshold at the same adjusted pulse width setting, i.e., 0.06 ms. If neither an increase in the pacing threshold nor a decrease in the pacing threshold is determined to occur during delivery of the adjusted therapy, and therefore there is not a change in the pacing threshold, NO in Block 514, the device waits until the next detection period for determining the pacing threshold, i.e., one hour, Block 516. Once it is determined that the next detection period is identified, YES in Block 516, the adjusted pacing therapy is delivered Block 510, and the process is repeated. According to one embodiment, the device determines that either an increase in the pacing threshold or a decrease in the pacing threshold occurs if there is a one-step increase or a one-step decrease, respectively, in the current adjusted pacing threshold from a prior adjusted pacing threshold determination. According to one embodiment, a one-step increase or decrease in the pacing threshold corresponds to an increase or decrease of approximately one tenth of a volt, so that, for example, an increase from 0.1 volts to 0.2 volts would correspond to a one-step increase and a decrease from 0.2 volts to 0.1 volts would correspond to a one-step decrease.

Other changes in parameter can be utilized in Block 508. For example, according to another exemplary embodiment, the device changes a single parameter of the pacing therapy, such as the pulse width, from the 0.5 millisecond delivered once per day, utilized during normal pacing delivery, Blocks 502-506, to a pacing therapy having a pulse width of 0.06 milliseconds and delivered once per day, and so forth.

Once it is determined that the pacing threshold has either increased or decreased and therefore a change in the pacing threshold between a current and a previous measurement at the adjusted pulse width has occurred, YES in Block 514, the device determines that either hypokalemia or hyperkalemia is likely present, and an alert may be generated. For example, the device determines that if the change in pacing threshold was an increased change, YES in Block 518, hypokalemia is determined to be likely present, Block 520, and an alert may be generated and/or the determination of hypokalemia likely being present is stored either remotely or within the device. On the other hand, if the change in pacing threshold was a decreased change, NO in Block 518, hyperkalemia is determined to be likely present, Block 522, and an alert may be generated and/or the determination of hyperkalemia likely being present is stored either remotely or within the device. Prior to generating the alert, the device may verify the likelihood of the presence of hypokalemia or hyperkalemia using secondary parameters, such as changes in ECG, changes in electrograms, changes in impedance, or changes in heart sounds, etc. If the presence of hypokalemia or hyperkalemia is verified using one or more of the secondary parameters, an alert may also be generated to alert the patient and/or the physician.

Figure 10:
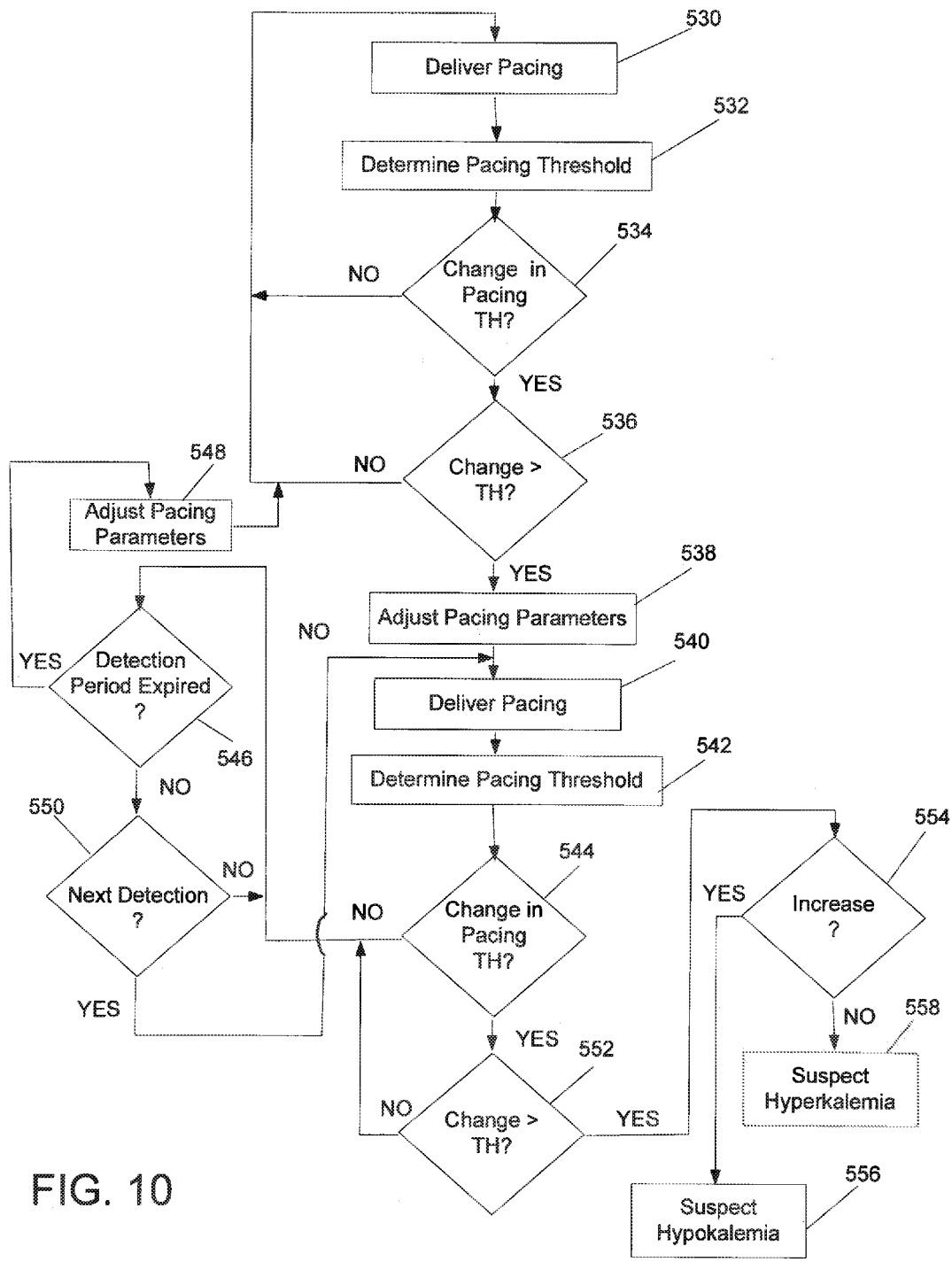
FIG. 10 is a flowchart of an exemplary method for monitoring cardiac function in a medical device according to an embodiment of the present disclosure.

FIG. 10 is a flowchart of an exemplary method for monitoring cardiac function in a medical device according to an embodiment of the present disclosure. As illustrated in FIG. 10, during normal delivery of pacing therapy by the device, i.e., when the device is not in the homeostasis variations detection mode, the device delivers pacing therapy using normal device programmed pacing parameters, Block 530. Once the pacing therapy is delivered, the device determines a current pacing therapy threshold, Block 532, and based on the current pacing therapy threshold, determines whether there has been a change in the pacing threshold, Block 534. Using the exemplary embodiment described above, during normal delivery, pacing therapy is delivered in Block 530 using a 0.5 millisecond pulse width, for example, and the device determines the current pacing therapy threshold in Block 532 at a rate of once per day, such as during the evening when the patient is assumed to be asleep.

In order to determine whether changes in the pacing threshold are occurring in Block 534, the device determines whether there is either an increase in the pacing threshold or a decrease in the pacing threshold by comparing the current determined pacing threshold to a prior determined pacing threshold associated with parameters of the current delivered pacing therapy, Block 530. If the pacing threshold has nether increased nor decreased, i.e., the current pacing threshold is neither greater than nor less than the prior determined pacing threshold, NO in Block 534, the device waits until the next scheduled determination of the pacing threshold (i.e., once per day for example) and the pacing threshold determination process is repeated. Once either the current pacing threshold is determined to be greater than the previous pacing threshold, indicating an increase in the pacing threshold, or the current pacing threshold is determined to be less than the previous pacing threshold, indicating a decrease in the pacing threshold, a change in the pacing threshold is determined, YES in Block 534, and the device determines whether the pacing threshold change is greater than a change threshold, Block 536, associated with parameters of the current delivered pacing therapy, Block 530.

According to an exemplary embodiment of the present disclosure, when not in the homeostasis mode, in order to determine whether the pacing threshold change is either greater than a change threshold, Block 536, the device determines whether there is a one-step or greater change in the current determined pacing threshold from the previously determined pacing threshold. If the change in pacing threshold is not greater than a one-step change, NO in Block 536, the device waits until the next scheduled determination of the pacing threshold (once per day, for example), and the pacing threshold determination process is repeated. If the change in pacing threshold is greater than the pacing threshold change threshold, YES in Block 536, the device advances to the homeostasis variations detection mode during which the device detects for the presence of homeostasis variations in the patient.

As described above, when in the homeostasis variations detection mode, Blocks 538-558, the device adjusts delivery of the pacing therapy, Block 538, delivers the adjusted pacing therapy, Block 540, and determines a pacing threshold associated with delivery of the adjusted pacing therapy, Block 542. During adjusting of the pacing therapy the device alters one or more of the pacing parameters, such as the pulse width and the rate at which the pacing therapy is delivered, for example. According to one exemplary embodiment, the device changes the pulse width and rate of delivery from the 0.5 millisecond delivered once per day, utilized during normal pacing delivery, Blocks 530-536, to a pulse width of 0.06 milliseconds and delivered every 15 minutes for one hour. Each time the pacing threshold associated with delivery of the adjusted pacing therapy is determined, Block 542, the device determines whether there has been a change in the pacing threshold in response to delivery of the adjusted pacing therapy, Block 544.

In particular, according to one embodiment of the present disclosure, while in the homeostasis variation detection mode, in order to determine whether there has been a change in the pacing threshold in response to delivery of the adjusted pacing therapy, Block 544, the device determines whether there has been either a predetermined increase in the pacing threshold when pacing therapy is delivered at the adjusted pulse width, or a predetermined decrease in the pacing threshold when pacing therapy is delivered at the adjusted pulse width, i.e., 0.6 ms, compared to a previous measurement at the adjusted pulse width. If neither an increase in the pacing threshold nor a decrease in the pacing threshold is determined to occur during delivery of the adjusted therapy and therefore there is not a change in the pacing threshold, NO in Block 544, the device determines whether the detection period, i.e., one hour, has expired Block 546. If the detection period has expired, YES in Block 546, the device transitions from the homeostasis detection mode, Blocks 538-558, back to the normal pacing therapy mode Blocks 530-536, adjusting the pacing parameters, Block 548, back to those previous utilized during normal pacing therapy, Blocks 530-536.

If the detection period has not expired, NO in Block 546, the device waits until the next detection period for determining the pacing threshold, i.e., 15 minutes, Block 550. Once it is determined that the next detection period is set to occur, YES in Block 550, the process is repeated with the adjusted pacing therapy being delivered, Block 540, and a determination being made as to whether changes in the pacing threshold associated with the delivered therapy occur, Blocks 542 and 544.

Once a change in the pacing threshold is determined to have occurred, YES in Block 544, the device determines whether the pacing threshold change is greater than a change threshold, Block 552, associated with the adjusted pacing parameters, Block 538. According to an exemplary embodiment of the present disclosure, while in the homeostasis mode, in order to determine whether the adjusted pacing threshold change is greater than a change threshold, Block 552, the device determines whether there is a four-step or greater change in the current determined pacing threshold from the previously determined pacing threshold. If the change in pacing threshold between a current pacing threshold and a previous pacing threshold determined at the adjusted pulse width, i.e., 0.6 ms, is not greater than the change threshold, NO in Block 552, the device determines whether the detection period, i.e., one hour, has expired Block 546, If the detection period has expired, YES in Block 546, the device transitions from the homeostasis detection mode, Blocks 538-558, back to the normal pacing therapy mode Blocks 530-536, adjusting the pacing parameters, Block 548, back to those previously utilized during normal pacing therapy, Blocks 530-536. If the detection period has not expired, NO in Block 546, the device waits until the next detection period for determining the pacing threshold, and the process is repeated as described above.

Once it is determined that the change in pacing threshold is greater than the change threshold, YES in Block 552, the device determines that either hypokalemia or hyperkalemia is likely present, and an alert may be generated and/or the determination of either hypokalemia or hyperkalemia likely being present is stored either remotely or within the device. For example, the device determines that if the change in pacing threshold was an increased change, YES in Block 554, hypokalemia is determined to be likely present, Block 556, and an alert may be generated, and/or the determination of hypokalemia likely being present is stored either remotely or within the device. On the other hand, if the change in pacing threshold was a decreased change, NO in Block 554, hyperkalemia is determined to be likely present, Block 558, and an alert may be generated and/or the determination of hyperkalemia likely being present is stored either remotely or within the device. Prior to generating the alert, the device may verify the likelihood of the presence of hypokalemia or hyperkalemia using secondary parameters, such as changes in ECG, changes in electrograms, changes in impedance, or changes in heart sounds, etc. If the presence of hypokalemia or hyperkalemia is verified using one or more of the secondary parameters, an alert may also be generated to alert the patient and/or the physician or the information may be stored.

It is understood that within the embodiments described, the device may look for one of an increase or a decrease in the pacing threshold being present during initial delivery of the pacing therapy when the device is not in the homeostasis mode, and whether hypokalemia or hypokalemia is determined to be present would depend on whether there is an increase or decrease subsequently determined while the device is in the homeostasis mode. For example, hypokalemia would be determined to be likely present if either an increase or a decrease is determined while the device is delivery normal pacing therapy while not in the homeostasis mode and it is determined that the pacing threshold subsequently is determined to increase while in the homeostasis mode. Similarly, hyperkalemia would be determined to be likely present if either an increase or a decrease in the pacing threshold is determined to be present during delivery of normal pacing therapy while the device is not in the homeostasis mode and the pacing threshold is subsequently determined to increase while in the homeostasis mode.

It is also understood that determining whether a decrease in the pacing threshold is greater than a threshold is typically related to an absolute value of the decrease in pacing threshold being greater than a threshold, and therefore refers to an absolute value of change, as is known in the art.

Thus, a medical device system and associated methods for detecting homeostasis variations for monitoring cardiac function have been presented in the foregoing description with reference to specific embodiments. It is understood that the various techniques and devices described may be implemented in any combination. It is appreciated that various modifications to the referenced embodiments may be made without departing from the scope of the disclosure as set forth in the following claims.

We claim:

1. A medical device for monitoring cardiac function in a patient, comprising:
   a plurality of electrodes to deliver cardiac pacing therapy; and
   a processor configured to determine a pacing threshold in response to initial delivery of the pacing therapy, determine whether there is a change in the pacing threshold during initial delivery of the pacing therapy, adjust a delivery parameter of the pacing therapy in response to determining the change in the pacing threshold during initial delivery of the pacing therapy, determine whether there is an increase in the pacing threshold during delivery of the adjusted pacing therapy, and determine hypokalemia in response to the increase in the pacing threshold during delivery of the adjusted pacing therapy being present.

2. The medical device of claim 1, wherein adjusting a delivery parameter of the pacing therapy comprises adjusting a pulse width and a rate of delivery of the pacing therapy.

3. The medical device of claim 2, wherein the pulse width is approximately 0.5 milliseconds and the rate of delivery is approximately once per day during initial deliver of the pacing therapy, and the pulse width is approximately 0.06 milliseconds and the rate of delivery is approximately once per hour during delivery of the adjusted pacing therapy.

4. The medical device of claim 1, wherein the determined increase in the pacing threshold during delivery of the adjusted pacing therapy is not equal to the determined change in the pacing threshold during initial delivery of the pacing therapy.

5. The medical device of claim 1, wherein the determined change in the pacing threshold during initial delivery of the pacing therapy comprises a one-step change.

6. The medical device of claim 1, wherein the determined increase in the pacing threshold during delivery of the adjusted pacing therapy comprise a four-step increase.

7. The medical device of claim 1, wherein the determined change in the pacing threshold during initial delivery of the pacing therapy comprises a one-step change and the determined increase in the pacing threshold during delivery of the adjusted pacing therapy comprises a four-step increase.

8. The medical device of claim 7, wherein the pulse width is approximately 0.5 milliseconds and the rate of delivery is approximately once per day during initial deliver of the pacing therapy, and the pulse width is approximately 0.06 milliseconds and the rate of delivery is approximately once per hour during delivery of the adjusted pacing therapy.

9. The medical device of claim 7, wherein adjusting a delivery parameter of the pacing therapy comprises adjusting a pulse width and a rate of delivery of the pacing therapy.

10. The medical device of claim 1, wherein the processor is further configured to determine whether there is a decrease in the pacing threshold during delivery of the adjusted pacing therapy, and determine hyperkalemia in response to the decrease in the pacing threshold during delivery of the adjusted pacing therapy being present.

11. The medical device of claim 1, wherein the processor is configured to generate an alert in response to the determined hypokalemia.

12. A method of monitoring cardiac function in a patient, comprising:
    delivering cardiac pacing therapy;
    determining a pacing threshold in response to initial delivery of the pacing therapy;
    determining whether there is a change in the pacing threshold during initial delivery of the pacing therapy;
    adjusting a delivery parameter of the pacing therapy in response to determining the change in the pacing threshold during initial delivery of the pacing therapy being present;
    determining whether there is an increase in the pacing threshold during delivery of the adjusted pacing therapy; and
    determining hypokalemia in response to the increase in the pacing threshold during delivery of the adjusted pacing therapy being present.

13. The method of claim 12, wherein adjusting a delivery parameter of the pacing therapy comprises adjusting a pulse width and a rate of delivery of the pacing therapy.

14. The method of claim 13, wherein the pulse width is approximately 0.5 milliseconds and the rate of delivery is approximately once per day during initial deliver of the pacing therapy, and the pulse width is approximately 0.06 milliseconds and the rate of delivery is approximately once per hour during delivery of the adjusted pacing therapy.

15. The method of claim 12, wherein the determined increase in the pacing threshold during delivery of the adjusted pacing therapy is not equal to the determined change in the pacing threshold during initial deliver of the pacing therapy.

16. The method of claim 12, wherein the change in the pacing threshold during initial deliver of the pacing therapy comprises a one-step change.

17. The method of claim 12, wherein the increase in the pacing threshold during delivery of the adjusted pacing therapy comprises a four-step increase.

18. The method of claim 12, wherein the change in the pacing threshold during initial deliver of the pacing therapy comprises a one-step change and the increase in the pacing threshold during delivery of the adjusted pacing therapy comprises a four-step increase.

19. The method of claim 18, wherein the pulse width is approximately 0.5 milliseconds and the rate of delivery is approximately once per day during initial deliver of the pacing therapy, and the pulse width is approximately 0.06 milliseconds and the rate of delivery is approximately once per hour during delivery of the adjusted pacing therapy.

20. The method of claim 18, wherein adjusting a delivery parameter of the pacing therapy comprises adjusting a pulse width and a rate of delivery of the pacing therapy.

21. The method of claim 12, further comprising generating an alert in response to the determined hypokalemia.

22. The method of claim 12, further comprising:
    determining whether there is a change in the pacing threshold during initial delivery of the pacing therapy;
    adjusting a delivery parameter of the pacing therapy in response to determining whether there is a first decrease;
    determining whether there is a second decrease in the pacing threshold during delivery of the adjusted pacing therapy; and
    determining hyperkalemia in response to the second decrease in the pacing threshold being present.

23. A non-transitory computer-readable medium for storing a set of instructions for performing a method, the method comprising:
    delivering cardiac pacing therapy;
    determining a pacing threshold in response to initial delivery of the pacing therapy;
    determining whether there is a change in the pacing threshold during initial delivery of the pacing therapy;
    adjusting a delivery parameter of the pacing therapy in response to determining the change in the pacing threshold during initial delivery of the pacing therapy being present;
    determining whether there is an increase in the pacing threshold during delivery of the adjusted pacing therapy; and
    determining hypokalemia in response to the increase in the pacing threshold during delivery of the adjusted pacing therapy being present.

* * * * *